(12) United States Patent
Bahney

(10) Patent No.: US 8,435,237 B2
(45) Date of Patent: May 7, 2013

(54) POLYP ENCAPSULATION SYSTEM AND METHOD

(75) Inventor: Timothy J. Bahney, Portland, OR (US)

(73) Assignee: Covidien LP, Mansfield, MA (US)

( * ) Notice: Subject to any disclaimer, the term of this patent is extended or adjusted under 35 U.S.C. 154(b) by 380 days.

(21) Appl. No.: 12/356,650

(22) Filed: Jan. 21, 2009

(65) Prior Publication Data

US 2009/0192510 A1    Jul. 30, 2009

Related U.S. Application Data

(60) Provisional application No. 61/024,289, filed on Jan. 29, 2008.

(51) Int. Cl.
*A61B 18/18* (2006.01)
*A61B 17/24* (2006.01)
*A61B 17/26* (2006.01)

(52) U.S. Cl.
USPC ........................ 606/45; 606/113; 606/114

(58) Field of Classification Search .......... 606/106, 606/110, 113, 114, 213, 45–47
See application file for complete search history.

(56) References Cited

U.S. PATENT DOCUMENTS

| 2,054,149 A | 9/1936 | Wappler |
| 3,631,363 A | 12/1971 | Miller |
| 4,196,734 A | 4/1980 | Harris |
| 4,397,313 A | 8/1983 | Vaguine |
| 4,462,412 A | 7/1984 | Turner |
| 4,493,320 A | 1/1985 | Treat |
| 4,503,855 A | 3/1985 | Maslanka |
| 4,553,393 A | 11/1985 | Ruoff |
| 4,572,190 A | 2/1986 | Azam et al. |
| 4,615,330 A | 10/1986 | Nagasaki et al. |
| 4,798,215 A | 1/1989 | Turner |
| 4,905,691 A | 3/1990 | Rydell |
| 5,078,716 A | 1/1992 | Doll |
| 5,097,844 A | 3/1992 | Turner |
| 5,158,561 A | 10/1992 | Rydell et al. |

(Continued)

FOREIGN PATENT DOCUMENTS

| DE | 390937 | 3/1924 |
| DE | 1099658 | 2/1961 |

(Continued)

OTHER PUBLICATIONS

U.S. Appl. No. 08/483,742, filed Jun. 7, 1995.

(Continued)

*Primary Examiner* — Matthew F Desanto

(57) ABSTRACT

An endoscopic electrosurgical instrument is presented for encapsulating and resecting biologic tissue, such as a polyp, from an anatomical structure, such as a lumen. The instrument includes an encapsulation assembly which includes a snare coupled to an electrically non-conductive, shrinkable pouch in a drawstring-like configuration. The encapsulation assembly may be folded within the elongated cylindrical housing of the endoscopic instrument, positioned within the patient at the surgical site, and deployed for use. Once positioned over the polyp, the snare is tightened around the peduncle thereof, and the pouch is activated, thereby shrinking and encapsulating the polyp. The polyp may then be resected using conventional or electrosurgical techniques. The disclosed instrument may include surgical tools and/or electrosurgical electrodes for performing surgical procedures. The disclosed system may reduce the occurrence of undesirable arcing and may aid retrieval of resected tissue.

20 Claims, 10 Drawing Sheets

U.S. PATENT DOCUMENTS

| | | |
|---|---|---|
| 5,190,542 A | 3/1993 | Nakao et al. |
| 5,207,675 A | 5/1993 | Canady |
| 5,330,483 A | 7/1994 | Heaven et al. |
| 5,336,227 A * | 8/1994 | Nakao et al. .................. 606/114 |
| 5,417,210 A | 5/1995 | Funda et al. |
| 5,465,731 A | 11/1995 | Bell et al. |
| 5,486,182 A | 1/1996 | Nakao et al. |
| 5,540,683 A | 7/1996 | Ichikawa et al. |
| 5,611,803 A | 3/1997 | Heaven et al. |
| 5,647,372 A | 7/1997 | Trovey et al. |
| 5,759,187 A | 6/1998 | Nakao et al. |
| 5,788,710 A | 8/1998 | Bates et al. |
| 5,906,620 A | 5/1999 | Nakao et al. |
| 5,916,235 A | 6/1999 | Guglielmi |
| 5,957,932 A | 9/1999 | Bates et al. |
| 5,961,526 A | 10/1999 | Chu et al. |
| 5,971,995 A | 10/1999 | Rousseau |
| 6,031,375 A | 2/2000 | Atalar et al. |
| 6,050,995 A | 4/2000 | Durgin |
| 6,068,603 A | 5/2000 | Suzuki |
| 6,071,281 A | 6/2000 | Burnside et al. |
| 6,096,053 A | 8/2000 | Bates et al. |
| 6,123,665 A | 9/2000 | Kawano |
| 6,216,044 B1 | 4/2001 | Kordis |
| 6,221,039 B1 | 4/2001 | Durgin et al. |
| 6,245,089 B1 | 6/2001 | Daniel et al. |
| 6,264,663 B1 | 7/2001 | Cano |
| 6,264,664 B1 | 7/2001 | Avellanet |
| 6,267,760 B1 | 7/2001 | Swanson |
| 6,344,026 B1 | 2/2002 | Burbank et al. |
| 6,346,116 B1 | 2/2002 | Brooks et al. |
| 6,350,267 B1 | 2/2002 | Stefanchik |
| 6,375,606 B1 | 4/2002 | Garibaldi et al. |
| 6,419,679 B1 | 7/2002 | Dhindsa |
| 6,468,272 B1 | 10/2002 | Koblish et al. |
| 6,494,885 B1 | 12/2002 | Dhindsa |
| 6,506,166 B1 * | 1/2003 | Hendler et al. ................ 600/562 |
| 6,517,538 B1 | 2/2003 | Jacob et al. |
| 6,517,539 B1 | 2/2003 | Smith et al. |
| 6,537,273 B1 | 3/2003 | Sosiak et al. |
| 6,551,327 B1 | 4/2003 | Dhindsa |
| 6,603,994 B2 | 8/2003 | Wallace et al. |
| 6,692,445 B2 | 2/2004 | Roberts et al. |
| 6,725,080 B2 | 4/2004 | Melkent et al. |
| 6,743,237 B2 | 6/2004 | Dhindsa |
| 6,773,432 B1 | 8/2004 | Clayman et al. |
| 6,786,905 B2 | 9/2004 | Swanson et al. |
| 6,972,017 B2 | 12/2005 | Smith et al. |
| 6,986,774 B2 | 1/2006 | Middleman et al. |
| 7,052,489 B2 | 5/2006 | Griego et al. |
| 7,115,125 B2 | 10/2006 | Nakao et al. |
| 7,135,018 B2 | 11/2006 | Ryan et al. |
| 7,439,736 B2 | 10/2008 | Meaney et al. |
| 7,467,015 B2 | 12/2008 | Van der Weide |
| 7,565,207 B2 | 7/2009 | Turner et al. |
| 2002/0022836 A1 | 2/2002 | Goble et al. |
| 2002/0049442 A1 | 4/2002 | Roberts et al. |
| 2004/0059345 A1 | 3/2004 | Nakao et al. |
| 2004/0097805 A1 | 5/2004 | Verard et al. |
| 2004/0242992 A1 | 12/2004 | Hareyama |
| 2005/0043750 A1 | 2/2005 | Scott, III et al. |
| 2005/0165411 A1 | 7/2005 | Orban, III |
| 2006/0229639 A1 | 10/2006 | Whitefield |
| 2007/0078459 A1 | 4/2007 | Johnson et al. |
| 2007/0173798 A1 | 7/2007 | Adams et al. |
| 2007/0179458 A1 | 8/2007 | Leroy et al. |
| 2007/0198011 A1 | 8/2007 | Sugita |
| 2007/0208339 A1 | 9/2007 | Arts et al. |
| 2007/0270794 A1 | 11/2007 | Anderson et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 467 501 | 4/1991 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 0 930 048 | 10/1998 |
| EP | 1 159 926 | 5/2001 |
| EP | 1 278 007 | 1/2003 |
| EP | 1 559 377 | 1/2005 |
| EP | 1 656 900 | 11/2005 |
| EP | 1 769 766 | 9/2006 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2007082675 | 4/2007 |
| SU | 166452 | 11/1964 |
| SU | 401367 | 11/1974 |
| SU | 727201 | 4/1980 |
| WO | 93/21845 | 11/1993 |

| WO | WO97/41924 | 11/1997 |
| WO | WO97/43971 | 11/1997 |
| WO | 99/04704 | 2/1999 |
| WO | 00/12010 | 3/2000 |
| WO | WO00/48672 | 8/2000 |
| WO | WO00/51513 | 9/2000 |
| WO | WO01/01847 | 1/2001 |
| WO | 01/35831 | 5/2001 |
| WO | WO01/74252 | 10/2001 |
| WO | WO02/45790 | 6/2002 |
| WO | WO02/061880 | 8/2002 |
| WO | WO 2004/004789 | 1/2004 |
| WO | WO2004/112628 | 12/2004 |
| WO | WO2005/016119 | 2/2005 |
| WO | 2005/112783 | 12/2005 |

OTHER PUBLICATIONS

U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.

Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/ Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSure™ " Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw•Hill, vol. 111, (1984), pp. 2490-2499.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages, 2003.

Esterline, "Light Key Projection Keyboard" 2004 Advanced Input Systems, located at: <http://www.advanced-input.com/lightkey> last visited on Feb. 10, 2005.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Johnson et al., "Evaluation of a Bipolar Electrothermal Vessel Sealing Device in Hemorrhoidectomy" Sales/Product Literature, Jan. 2004.

Jarrett et al., "Use of the LigaSure™ Vessel Sealing System for Peri-Hilar Vessels in Laparoscopic Nephrectomy" Sales/Product Literature 2000.

Johnson, "Evaluation of the LigaSure™ Vessel Sealing System in Hemorrhoidectormy" American College of Surgeons (ACS) Clinic La Congress Poster (2000).

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General , Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics Figo World Congress 2000, Washington, DC.

MDTECH product literature (Mar. 2000) I'D Wire: product description, 1 page.

MDTECH product literature (Dec. 1999) "FlexStrand": product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Oapril 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Stuart W. Young, Nuclear Magnetic Resonance Imaging—Basic Principles, Raven Press, New York, 1984.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817•825.

S. Humphries Jr. et al., "Finite•Element Codes to Model Electrical Heating and Non•LInear Thermal Transport in Biological Media", Proc. ASME HTD-355, 131 (1997).

Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.

Urrutia et al., (1988). "Retractable-Barb Needle for Breast Lesion Localization: Use in 60 Cases," Radiology 169(3):845-847.

Valleylab Brochure, "Valleylab Electroshield Monitoring System" 2 pages, Nov. 1995.

ValleyLab Brochure, "Electosurgery: A Historical Overview", Innovations in Electrosurgery, 1999.

Vallfors et al., "Automatically Controlled Bipolar Electrocoagulation—'COA-COMP'" Neurosurgical Review 7:2-3 (1984) pp. 187-190.

W. Scott Helton, "LigaSure™ Vessel Sealing System: Revolutionary Hemostasis Product for General Surgery" Sales/Product Literature 1999.

Wald et al., "Accidental Burns", JAMA, Aug. 16, 1971, vol. 217, No. 7, pp. 916-921.

Walt Boyles, "Instrumentation Reference Book", 2002, Butterworth-Heinemann, pp. 262-264.

http://www.ultimateniti.com/, Ultimate NiTi Technologies, Document Center, Standard Terms and Definitions, 2004.

http://www.ultimateniti.com/, Ultimate NiTi Technologies, Document Center, The Basics of Shape Memory, 2004.

http://www.ultimateniti.com/, Ultimate NiTi Technologies, Document Center, The Basics of Super-Elasticity, 2004.

http://www.ultimateniti.com/, Ultimate NiTi Technologies, Document Center, Effects of Heat Treating, 2004.

http://www.ultimateniti.com/, Ultimate NiTi Technologies, Document Center, Inherent Properties of Nickel Titanium, 2004.

http://www.ultimateniti.com/, Ultimate NiTi Technologies, Document Center, Comparuson—NiTi vs Stainless Steel, 2004.

http://www.ultimateniti.com/, Ultimate NiTi Technologies, Document Center, Joining Methods for NiTi Components, 2004.

http://www.ultimateniti.com/, Ultimate NiTi Technologies, Document Center, Joining Method for NiTi Components, 2004.

European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.4 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 09151621 dated Jun. 18, 2009.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.

International Search Report PCT/US98/18640 dated Jan. 29, 1998.
International Search Report PCT/US98/23950 dated Jan. 14, 1998.
International Search Report PCT/US99/24869 dated Feb. 11, 2000.
Esterline Product Literature, "Light Key: Visualize a Virtual Keyboard. One With No Moving Parts", Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
EPO Communication dated Jan. 24, 2012 in related European Appln. No. 09 151 621.

* cited by examiner

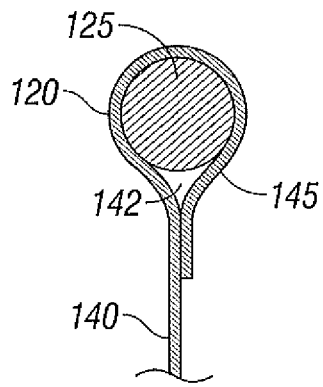
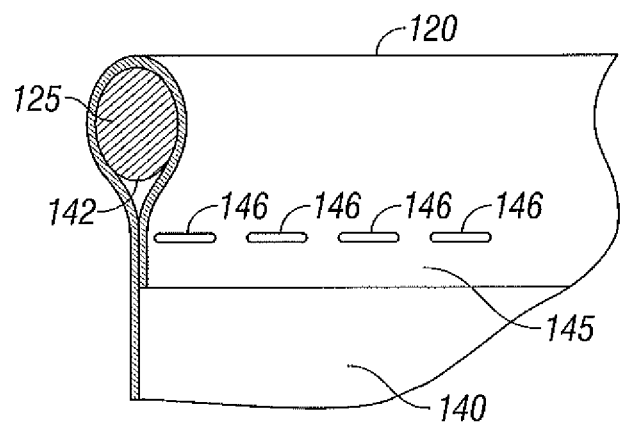
FIG. 5A  FIG. 5B
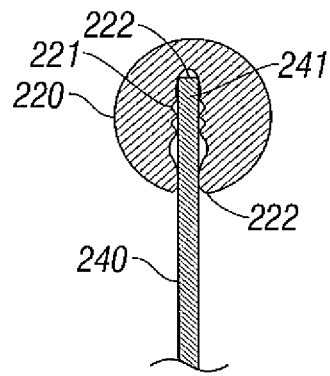
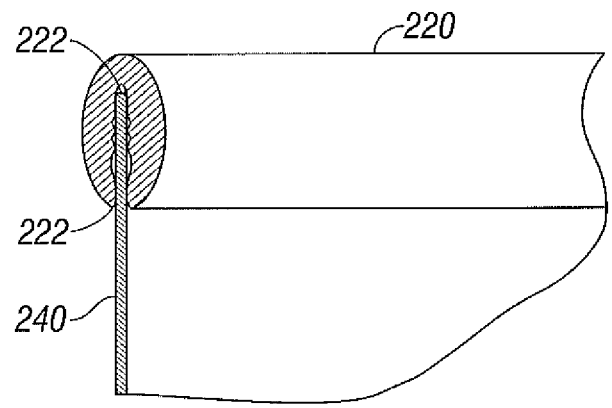
FIG. 6A  FIG. 6B
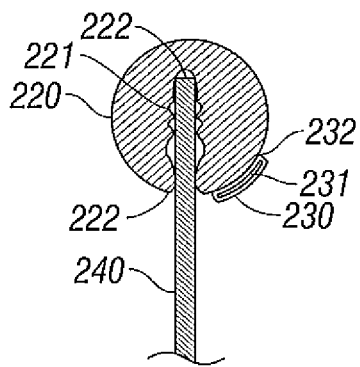
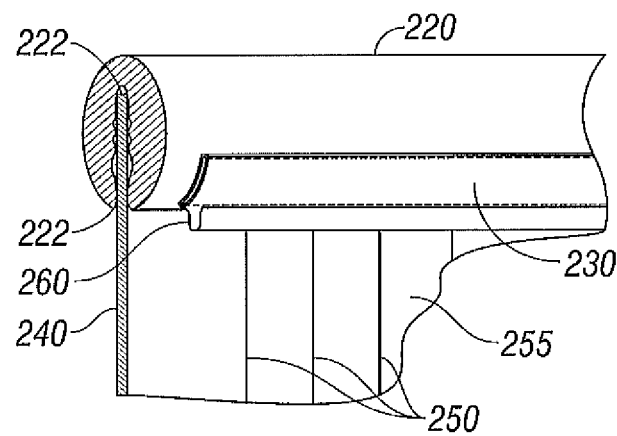
FIG. 7A  FIG. 7B

POLYP ENCAPSULATION SYSTEM AND METHOD

CROSS-REFERENCE TO RELATED APPLICATIONS

This application claims the benefit of priority to U.S. Provisional Application Ser. No. 61/024,289 entitled "POLYP ENCAPSULATION SYSTEM AND METHOD" filed Jan. 29, 2008 by Timothy J. Bahney, which is incorporated by reference herein.

BACKGROUND

1. Field of the Disclosure

The present disclosure relates to instruments for performing minimally invasive surgical procedures. More particularly, the present disclosure relates to an endoscopic electrosurgical instrument for encapsulating and resecting biologic tissue, such as a polyp, that includes a shrinkable pouch for isolating the tissue undergoing resection from the surrounding luminal walls or other adjacent tissue.

2. Background of Related Art

Minimally invasive surgical techniques have been developed wherein the surgical site is accessed by instruments inserted through small incisions in the body, as compared to traditional open surgical procedures where much larger incisions are required to expose the surgical site. Minimally invasive surgical procedures, also known generally as laparoscopic or endoscopic procedures, are often performed in conjunction with electrosurgical techniques. Throughout the present disclosure, the term "minimally invasive" should be understood to encompass both endoscopic and laparoscopic procedures, and the terms "minimally invasive", "endoscopic", and "laparoscopic" are to be construed equivalently. Minimally invasive surgical procedures are performed through access devices such as a cannula that is inserted percutaneously into a patient's body. The cannula has a central opening through which surgical objects are introduced and manipulated during the course of the procedure.

Electrosurgical techniques employ radiofrequency (RF) electrical signals in the approximately 200 kHz-3.3 mHz range in connection with surgical instruments, to cut, ablate, or coagulate biologic tissue endogenically. Typically, electrosurgical signals are operated at 100% duty cycle for maximal cutting effect, and are pulse modulated at duty cycles ranging from 50% to 25% for less aggressive cutting, also referred to as blending, or, at a substantially lower duty cycle of approximately 6%, for coagulating. The electrosurgical signal can be applied to the patient via electrodes in either bipolar mode, or monopolar mode. In bipolar mode, both the active and return electrodes are at the surgical site, effectuated by, for example, both jaws of a pair of forceps, such that the electrosurgical signal passes through only the tissue that is held between the jaws of the instrument. In monopolar mode, the active electrode is the surgical instrument at the surgical site, and the return electrode is elsewhere on the patient, such that the electrosurgical signal passes through the patient's body from the surgical site to the return electrode.

Snares are a class of surgical instruments used in the resection of tumors and polyps, particularly those situated on the inner walls of a lumen such as an esophagus, colon, intestine, urethra, blood vessel, or other tubular anatomic structure. Typically, the instrument has at its distal end a wire loop that is positioned around the base or peduncle of the polyp. A pouch or mesh basket for capturing the resected tissue may optionally be attached circumferentially to the wire loop. The proximal end of the instrument is coupled to a source of electrosurgical energy, such as an electrosurgical generator. After the snare is positioned, the surgeon actuates a control on the instrument which causes the wire loop to tighten around the polyp in a drawstring fashion. The surgeon then actuates a second control, typically a handswitch or footswitch, which causes electrosurgical energy to be applied through the wire loop to the operative site, which severs the polyp from the underlying tissue by electrosurgical cutting.

Electrosurgical snares that perform the described technique may have drawbacks. For example, when a particularly large or irregularly shaped polyp is resected, uncontrolled arcing can occur between the polyp and the opposing lumen wall, between the polyp and another anatomical structure located near the polyp, or between the polyp and bodily fluids at the operative site. The uncontrolled dispersion of electrosurgical energy through arcing is undesirable, as it can cause the cutting operation to fail, can cause harmful burns to the opposing lumen wall or other anatomical structures, and can lead to increased operative times and impaired patient outcomes.

SUMMARY

The present disclosure provides a wire loop snare that includes an electrically non-conductive shrinkable pouch attached thereto. The pouch encapsulates and electrically insulates the polyp being resected from surrounding tissue and/or bodily fluids. By insulating the polyp during the electrosurgical procedure, the uncontrolled dispersion of electrosurgical energy is prevented, thereby reducing the risk of arcing. Encapsulation of the polyp may also prevent the inadvertent spread of malignant or pathogenic cells from the polyp.

The insulating shrinkable pouch may have several benefits. Bodily fluids which may remain trapped in the pouch may provide an undesirable return path for electrosurgical energy, which in turn may cause arcing. By shrinking the pouch around the polyp, voids and gaps which may exist between the polyp and pouch are collapsed, which causes bodily fluids in the pouch to be forced out, thereby eliminating a source of arcing and/or short-circuiting of the electrosurgical energy. Moreover, the shrinking pouch may reduce the size of the polyp and increase clearance between the polyp and surrounding tissue, which may also decrease the risk of arcing. Additionally, reducing the size of the polyp in accordance with the present disclosure can facilitate retrieval and removal of the polyp. It is envisioned the pouch may be constructed of any suitable shrinkable material now or in the future known, including without limitation heat-shrinkable material, electrically-shrinkable material, and/or chemically-shrinkable material.

In accordance with the present disclosure, the wire loop snare is slidably affixed to the pouch circumferentially at its opening to enable the proximal ends of the wire loop to be pulled in a drawstring-like fashion, thus enabling the surgeon to tighten the snare around, for example, the base of a polyp. There is disposed at the pouch opening a generally tubular channel through which the wire loop snare passes. The wire loop is formed by a first wire and a second wire for providing activation current to the at least one activating element as will be further described below. The first and second wires are joined at their respective termini by an insulating member, located preferably at the distal end of the loop. The first and second wires are coupled to the at least one activating element at a location that is preferably substantially adjacent to the termini of the first and second wires, respectively.

In one embodiment, the pouch is constructed of a heat-shrinkable material. Incorporated within the pouch material are activating elements for heating and thus shrinking the pouch. In an embodiment the activating elements are electrical conductors, constructed from resistance wire material such as Nichrome or other suitable resistance material. The activating elements are configured to form a heating array using, for example, a parallel, serial or series-parallel arrangement as will be familiar to a person of ordinary skill in the art. The heating array is coupled to the first and second wires, which are, in turn, switchably coupled, or electro-operably coupled, to a source of activating energy, such as an electric current that is controlled by, for example, a handswitch or a footswitch. The wires may be coupled to the heating array at a point substantially adjacent to the distal end of the wire loop snare, however, other coupling points are contemplated within the scope of the present disclosure.

In another embodiment, the wire loop snare is an electrosurgical electrode for performing electrosurgical procedures such as cutting, blending and coagulation. The electrosurgical electrode wire is disposed along the edge of the pouch opening in an external drawstring configuration. The edge of the pouch is captured within a longitudinal slot formed by, for example, crimping the electrosurgical electrode around the edge of the pouch. First and second insulated conductor are provided on the outer surface of the electrode for activating the pouch heating array as previously described herein.

In an alternative embodiment, a shrinkable mesh pouch having a deactivated (i.e., "unshrunken") state and an activated (i.e., "shrunken") state for capturing the polyp is disclosed. The mesh pouch can be constructed of a shape memory alloy, such as Nitinol, which is configured to shrink upon activation for reducing the size of the polyp. By compressing the polyp, the mesh pouch increases clearance between the polyp and surrounding tissue, decreasing the risk of arcing and aiding retrieval as well.

The shrinkable wire mesh pouch can be configured by forming the wire mesh pouch from a suitable material, such as Nitinol mesh; annealing the pouch to define the austenite shape and size of the pouch corresponding to the activated state; and expanding the pouch to define the martensite size and shape corresponding to the deactivated state. The mesh pouch is initially provided to the surgical site in the martensite state. The mesh pouch is switchably coupled to a source of activating energy, such as an electric current that is controlled by, for example, a handswitch or a footswitch. The passage of electric current through the shape memory alloy material heats the material through its transformation temperature range, causing the pouch to revert to its austenite shape with significant force, thereby shrinking around, and encapsulating, the polyp.

It is further envisioned that the shrinkable wire mesh incorporates a membrane for isolating the polyp from surrounding tissue. Optionally or additionally, the membrane can be formed from electrically insulating material. In an embodiment, the membrane is integrally disposed upon the outer surface of the wire mesh pouch to electrically and/or thermally insulate the wire mesh from surrounding tissue and/or bodily fluids.

Also envisioned within the scope of the present disclosure is a surgical tool that is extendable from the instrument for performing additional or alternative treatment modalities at the operative site. In an embodiment, the surgical tool incorporates a cutting edge. Additionally or alternatively, the surgical tool is an electrosurgical electrode for performing electrosurgical cutting, blending and/or coagulating at the operative site.

Also disclosed is a system for electrosurgical polyp resection and retrieval that includes an electrosurgical instrument coupled to a source of electrosurgical energy, such as an electrosurgical generator. The instrument consists of an elongated tubular support member that includes at its proximal end a handle and controls, such as a handswitch, for deploying and actuating the snare, for causing the pouch to be shrunk, and for activating electrosurgical energy. Additionally or alternatively, at least one footswitch control may be used for causing the pouch to be shrunk and/or activating electrosurgical energy. At its distal end, the tubular member houses a wire loop snare electrode that includes a shrinkable pouch attached thereto, wherein the wire loop electrode is configured to have an extended and a retracted position. The distal end of the tubular member optionally has an electrosurgical electrode having an extended and a retracted position for cutting, blending and/or coagulating tissue at the operative site.

A method for encapsulating and resecting biologic tissue, such as a polyp, is disclosed that includes providing a wire loop snare having an electrically non-conducting, shrinkable pouch having an opening disposed circumferentially thereupon; positioning the snare over the polyp; tightening the snare around the base of the polyp in a drawstring fashion; shrinking the pouch to encapsulate and, optionally or alternatively, reduce the size of the polyp; providing an electrosurgical signal to the wire loop snare to sever the polyp from the underlying tissue; and withdrawing the pouch containing the resected tissue from the patient. The provided method can additionally include coagulating or cauterizing the operative site substantially concurrently with, or subsequent to, the step of severing the polyp.

Yet another method for encapsulating and resecting biologic tissue, such as a polyp, is disclosed that includes providing a wire loop snare having a shrinkable mesh pouch having an opening disposed circumferentially thereupon; positioning the snare over the polyp; tightening the snare around the base of the polyp in a drawstring fashion; shrinking the pouch to capture and, optionally or alternatively, reduce the size of the polyp, providing an electrosurgical signal to the wire loop snare to sever the polyp from the underlying tissue; and withdrawing the mesh pouch containing the resected tissue from the patient. The aforesaid method can additionally include coagulating or cauterizing the operative site substantially concurrently with, or subsequent to, the step of severing the polyp.

BRIEF DESCRIPTION OF THE DRAWINGS

Various embodiments of the present disclosure will be described herein below with reference to the figures wherein:

FIG. 5A is an axial cross sectional view of a polyp encapsulation snare in accordance with the present disclosure showing the wire loop drawstring attachment;

FIG. 5B is an oblique cross-sectional view of the wire loop drawstring attachment of FIG. 5A;

FIG. 6A is an axial cross sectional view of a polyp encapsulation snare in accordance with the present disclosure showing an electrosurgical electrode snare in an external drawstring arrangement;

FIG. 6B is an oblique cross sectional view of the external drawstring arrangement of the electrosurgical electrode snare of FIG. 6A;

FIG. 7A is an axial cross sectional view of a polyp encapsulation snare in accordance with the present disclosure showing an insulated conductor;

FIG. 7B is an oblique cross-sectional view of the wire an electrosurgical electrode snare of FIG. 7A showing the coupling of the insulated conductor to the heating array;

DETAILED DESCRIPTION

Figure 1A:
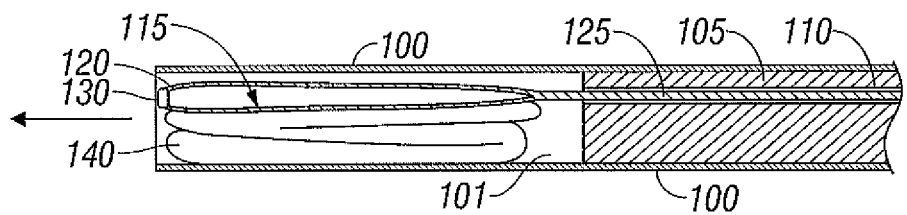
FIG. 1A is a side cross sectional view of one embodiment of a polyp encapsulation snare in accordance with the present disclosure showing the undeployed snare folded within a cylindrical housing.

Embodiments of the presently disclosed polyp encapsulation system and method are described herein in detail with reference to the drawings, in which like reference numerals designate identical or corresponding elements in each of the several views. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

Figure 1B:
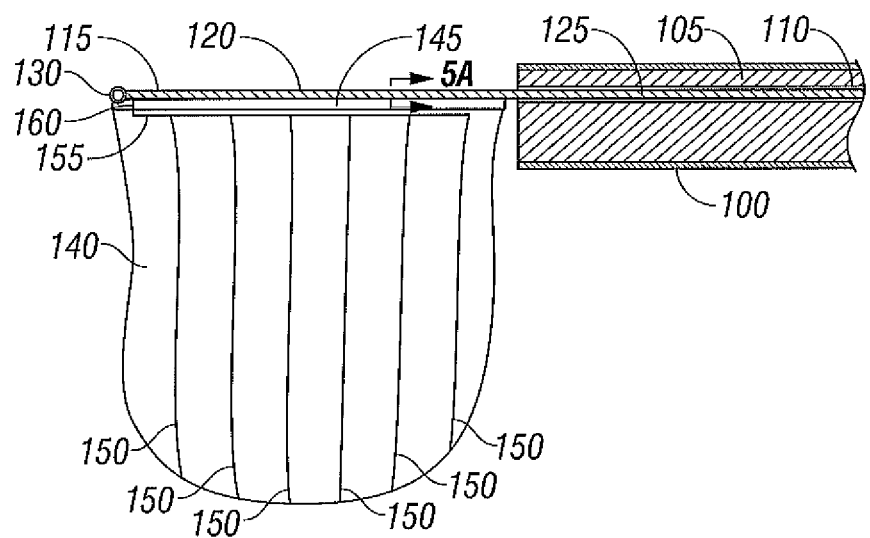
FIG. 1B is a side cross sectional view of the polyp encapsulation snare of FIG. 1A showing the snare in a deployed configuration.
Figure 2:
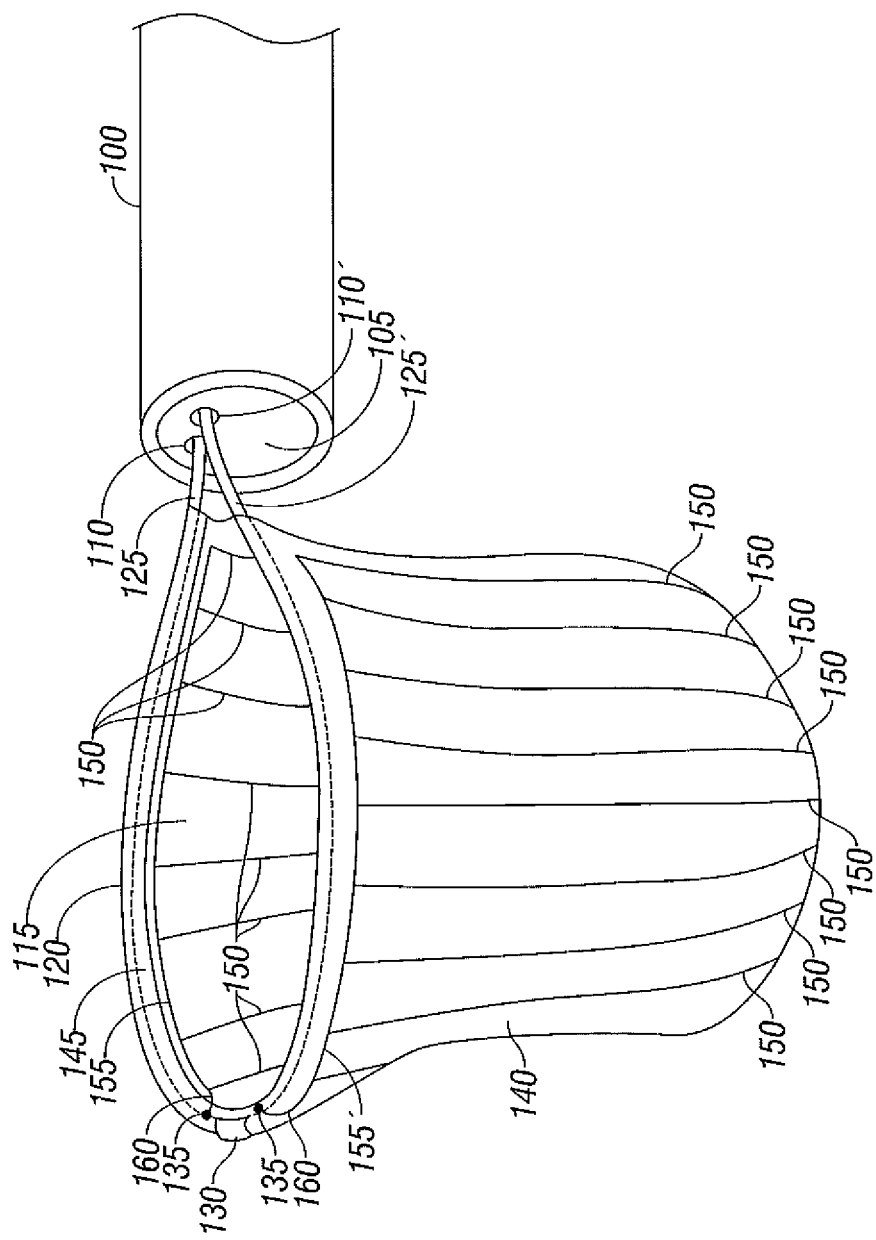
FIG. 2 is an oblique view of the polyp encapsulation snare of FIG. 1B.
Figure 3:
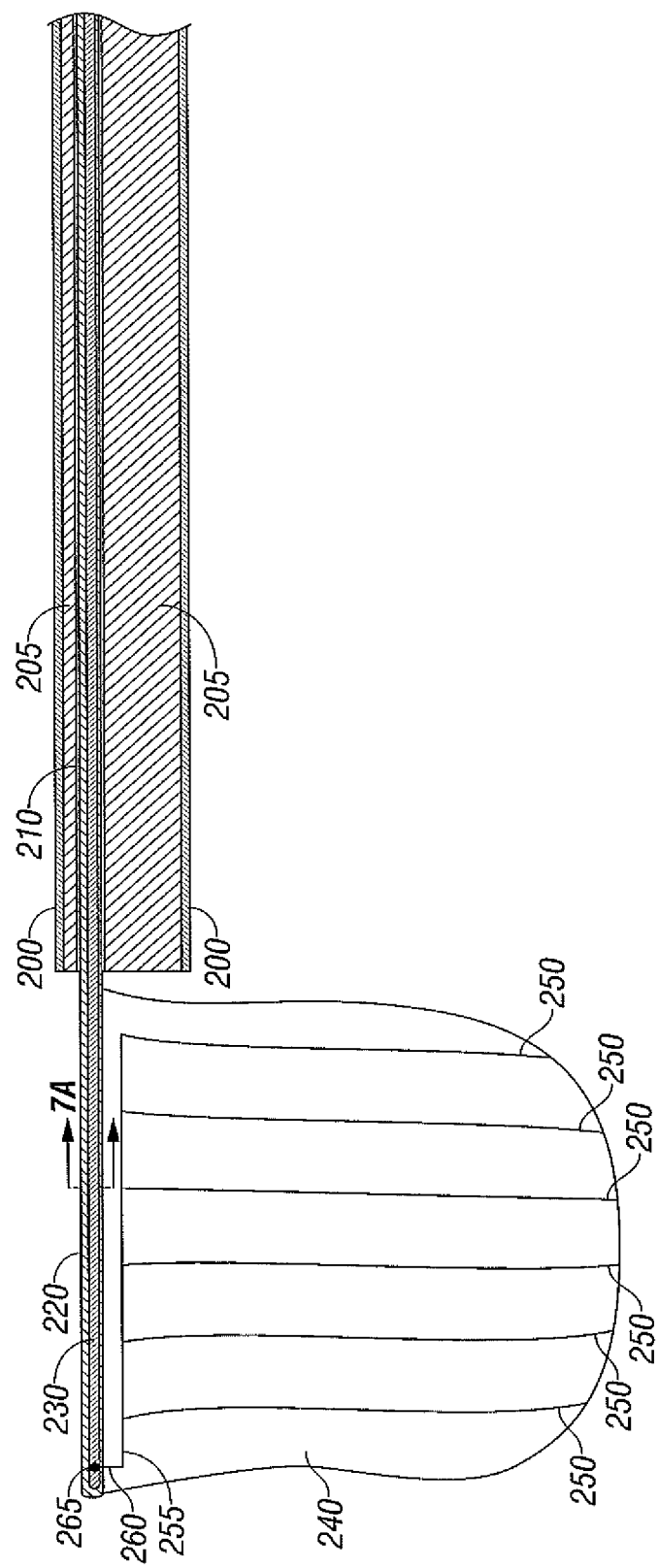
FIG. 3 is a side cross sectional view of another embodiment of a polyp encapsulation snare having an electrosurgical snare electrode in accordance with the present disclosure.
Figure 4:
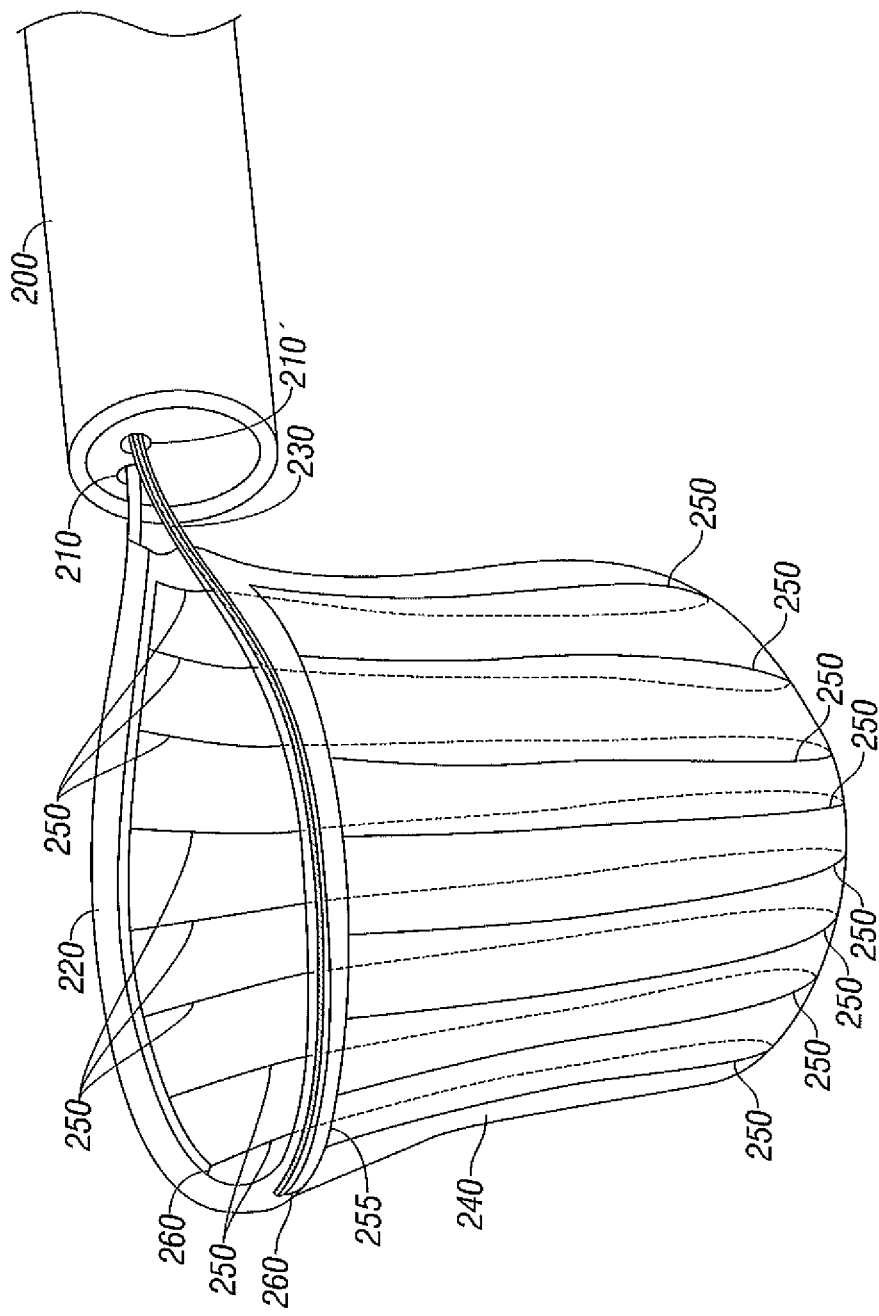
FIG. 4 is an oblique view of the polyp encapsulation snare of FIG. 3.

There is disclosed a polyp encapsulation device having a pouch that is shrinkable upon activation by a surgeon. Disposed circumferentially around the opening of the pouch is a wire loop snare for tightening the opening of the pouch around the polyp and for providing shrink activation energy, such as direct current electricity, alternating current electricity, or pulse-width modulated electrical current, to the pouch material. As illustrated in FIGS. 1A, 1B, and 2, an embodiment of a polyp encapsulation instrument 10 in accordance with the present disclosure includes a tubular housing 100, a support member 105 that is slidably disposed within the tubular housing 100, and a pouch assembly 115. The polyp encapsulation instrument 10 has an undeployed configuration and a deployed configuration, as illustrated by FIG. 1A and FIG. 1B, respectively. In the undeployed configuration, the sliding support member 105 is retracted within the tubular housing 100 forming a storage cavity 101 at the distal end thereof wherein the pouch assembly 115 may be stored in a generally folded, amorphous or irregularly-shaped configuration. The surgeon may introduce the instrument 10 to the surgical site in the undeployed configuration. Once positioned at the surgical site, the surgeon may actuate a deployment control, such as a hand lever (not shown), that causes support member 105 to slide distally which displaces the volume described by storage cavity 101, thereby deploying pouch assembly 115.

Pouch assembly 115 includes an electrically conductive wire loop snare 125, 125' having a proximal open end and a distal closed end, and a shrinkable pouch 140. Wire loop snare 125, 125' are joined at the distal closed end by insulating coupler 130. When snare assembly 115 is in the deployed configuration, the distal portions of wire loop snare 125, 125' assume a generally circular or semi-circular shape which describes the periphery of the opening of shrinkable pouch 140. Wire loop snare 125, 125' may be constructed of material having an elastic limit sufficient to enable stowage of the snare assembly 115 in storage cavity 101 as previously described herein, while remaining fully recoverable to the desired circular or semicircular share upon deployment. In an embodiment, wire loop snare 125, 125' can be constructed of stainless steel or Nitinol, for example. The open ends of wire loop snare 125, 125' communicate through at least one snare conduit 110, 110', respectively, that may be formed within sliding support member 105. Wire loop snare 125, 125' is operably coupled at the proximal ends thereof to a source of activation energy, and to a tightening control, such as a second hand lever (not explicitly shown), that is operable by the surgeon for tightening the snare 125, 125'. After the pouch is positioned over the target polyp, the surgeon may actuate the tightening control and cause the open ends of wire loops snare 125, 125' to be drawn in a proximal direction, thereby contracting the opening of the pouch around the base of the polyp.

During actuation of the deployment control, wire loop snare 120, 125' operates in a cooperative relationship with sliding member 105 for deployment such that wire loop snare 120, 125' and slidable member 105 move as a single unit with respect to tubular housing 100. Conversely, actuation of the tightening control causes wire loop snare 120, 125' to move independently with respect to stationary sliding member 105 and tubular housing 100 for tightening the snare 125, 125' around the polyp, as will be readily appreciated.

Wire loop snare 125, 125' are disposed circumferentially around the opening of shrinkable pouch 140 enclosed within a channel 142 described by a drawstring hem 120. As best illustrated in FIGS. 5A and 5B, drawstring hem 120 can be formed along the periphery of the opening of pouch 140 by rolled edge 145 of the pouch material. The resulting channel 142 is configured to allow movement of wire loop snare 125, 125' within drawstring hem 120, which thus facilitates tightening of the pouch assembly 115 around the targeted polyp. In an embodiment, channel 142 may be configured to provide frictional resistance to movement of wire loop snare 125, 125' to maintain the position of wire loop snare 125, 125' subsequent to tightening by the surgeon. Insulating coupler 130 is similarly disposed within channel 142. Rolled edge 145 may be secured to the pouch material by any suitable manner of bonding, for example, by stitches 146, by adhesive, and/or by heat welding.

In one embodiment, pouch 140 includes at least one heating element 150 for delivering thermal energy to the pouch 140 for effectuating shrinkage thereof. The heating elements can form a heating array for delivering heat in an essentially uniform manner throughout the pouch 140 to cause the pouch 140 to shrink at a substantially uniform rate. It may also be desirable to cause the pouch 140 to shrink in a non-uniform manner. For example, it may be desirable to shrink the open region 140 of the pouch at faster rate than the closed region of the pouch 140 in order to facilitate encapsulation and to avoid squeezing the polyp from the pouch. In an alternate embodiment, the heating array may be configured to deliver heat in a non-uniform manner. It is also contemplated that the pouch walls may have varying thickness, to further tailor the rate and amount of shrinkage. In yet another embodiment, the pouch 140 includes a plurality of independent shrinking regions that may be activated individually or in combination by the surgeon in order to achieve a particular desired operative result.

The heating elements 150 are electrically coupled to wire loop snare 125, 125' to form a series circuit, parallel circuit, series-parallel circuit, or other suitable circuit topology. Heating elements 150 may be constructed of any conductive substance, and may be constructed from resistance wire such as Nichrome for efficiently converting electrical energy into the thermal energy required to effectuate pouch shrinkage. In an embodiment, a heating array that includes heating elements 150 are coupled in parallel to a common conductor 155, 155', which, in turn, couple to wire loop snare 125, 125' by lead wires 160, 160', respectively, using any suitable type of connection, including crimping, soldering, and/or wire bonding. In an embodiment, common conductor 155, 155' may also be a heating element. The heating elements 150 are incorporated into the pouch material by, for example, lamination, weaving, adhesive, bonding, or molding. Embodiments are contemplated wherein the heating element 150, common conductor 155, 155', and/or lead wire 160 are printed on the pouch.

Pouch 140 may be constructed from any material having suitable heat-shrink properties, such as polyethylene or cross-linked polyolefin; mechanical properties, such as puncture resistance and tensile strength; and biocompatibility. The pouch may be constructed from material that is substantially opaque, or substantially translucent. Embodiments are also contemplated wherein the pouch is constructed of material that is substantially transparent, which may permit improved visualization of the operative site.

Another embodiment envisioned within the scope of the present disclosure is illustrated in FIGS. 3, 4, 6A, and 6B, wherein the wire loop snare is an electrosurgical electrode snare 220. A shrinkable pouch 240 is slidably captured within a longitudinal slot 222 provided by electrosurgical electrode snare 220. The slot 222 is configured to allow longitudinal movement of the pouch edge 241 with respect to the electrosurgical electrode snare 220, while concurrently resisting "pullout" of the pouch material, i.e., undesired movement of the pouch material in a direction orthogonal to the longitudinal axis of the electrosurgical electrode snare 220. By this arrangement, the electrosurgical electrode snare 220 may be tightened around the base of the polyp, causing the pouch material to slide within the groove, thereby effectuating ensnarement of the polyp within the pouch. The longitudinal slot 222 may include at least one internal longitudinal rib 221 configured to retain the pouch material and to resist pullout, while facilitating longitudinal movement of the electrosurgical electrode snare 220 with respect to the pouch 240. In an embodiment, the longitudinal slot 222 may be dimensioned to frictionally resist loosening of the electrosurgical electrode snare 220, or can be configured to minimize friction between the pouch edge 241 and slot 222. First and second insulated wires 230 are provided on the outer surface of electrosurgical electrode snare 220, preferably adjacent to and running substantially parallel to slot 222 for activating the pouch heating array as previously described herein. In an embodiment, the insulated wires 230 may have a substantially flat cross-section, as best illustrated in FIGS. 7A and 7B. Insulated wires 230 may be affixed to electrosurgical electrode 220 in any suitable manner, for example, by adhesive or heat welding, or formed in place, for example, by injection molding. The insulated wires 230 are switchably coupled at the proximal end of the instrument to a source of activating energy, such as an electric current that is controlled by, for example, a hand-switch or a footswitch. Insulated wires 230 are coupled to the pouch heating array 250, 255 by a lead 260 at a location substantially adjacent to the distal end of the electrosurgical electrode 220, however, other coupling points are contemplated within the scope of the present disclosure. Electrosurgical electrode 220 may be configured as a monopolar or bipolar electrosurgical electrode.

Figure 8A:
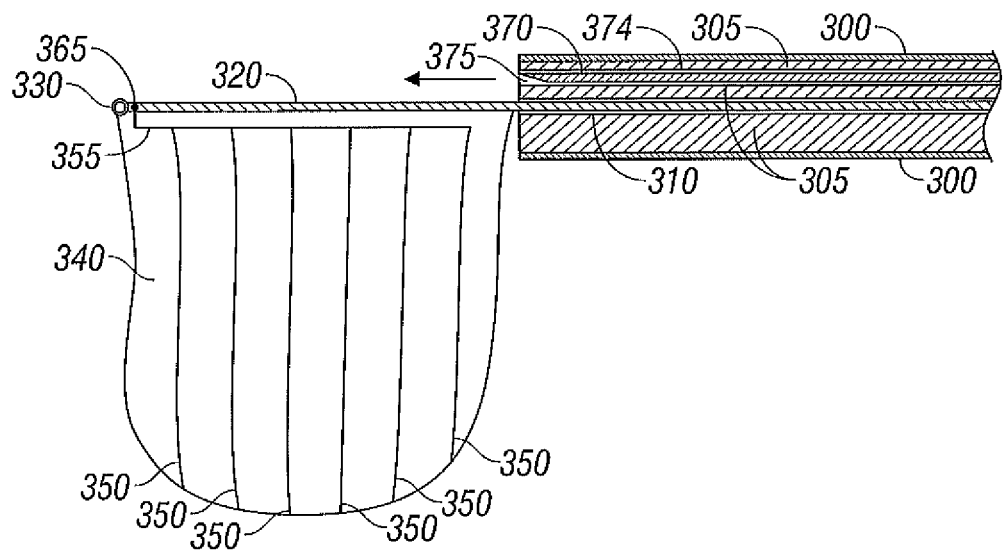
FIG. 8A is a side cross sectional view of still another embodiment of a polyp encapsulation snare in accordance with the present disclosure showing the surgical tool in a retracted configuration.
Figure 8B:
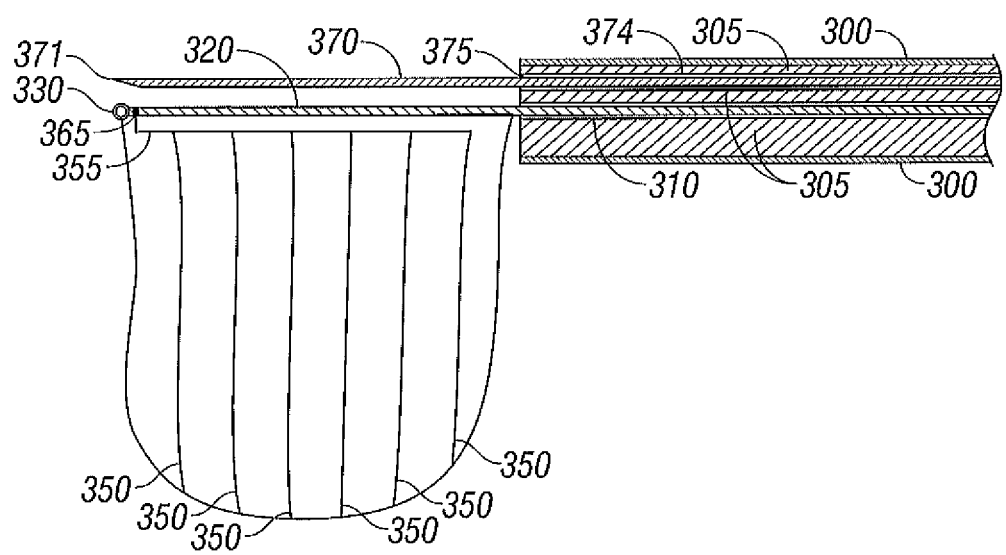
FIG. 8B is a side cross sectional view of the polyp encapsulation snare of FIG. 8A showing the surgical tool in an extended configuration.
Figure 9A:
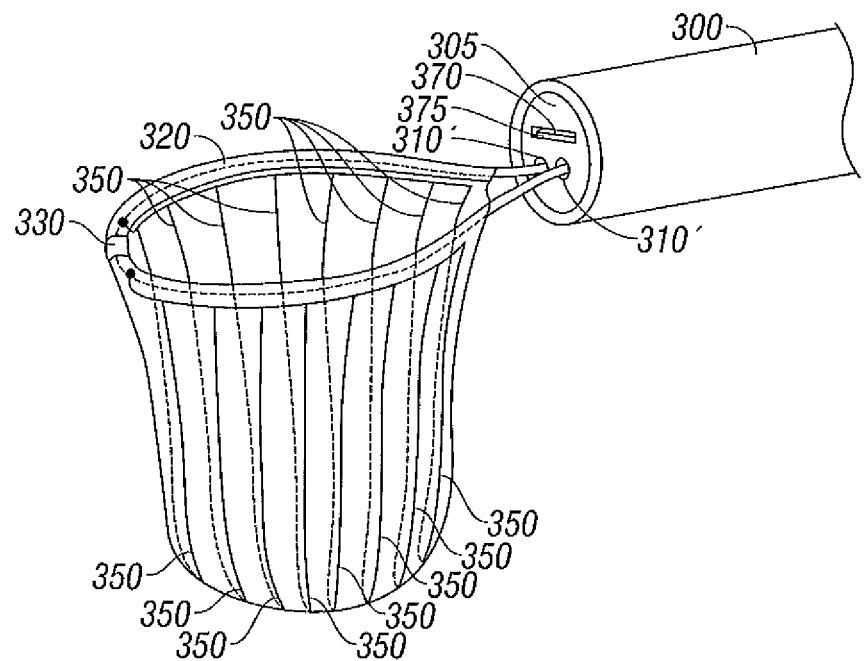
FIG. 9A is an oblique view of the polyp encapsulation snare of FIG. 5A showing the surgical tool in a retracted configuration.
Figure 9B:
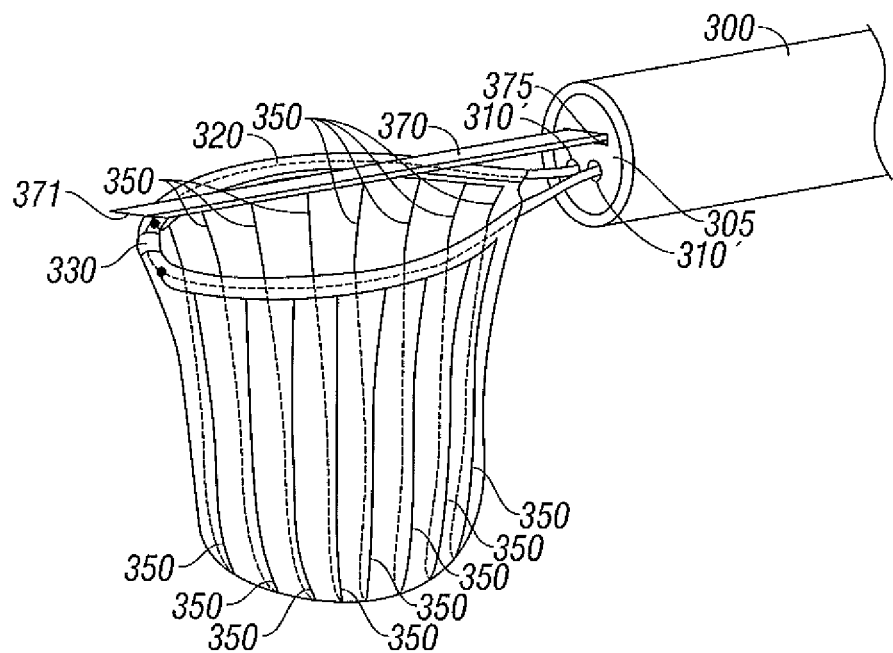
FIG. 9B is an oblique view of the polyp encapsulation snare of FIG. 8A showing the surgical tool in an extended configuration.

Yet another polyp encapsulation device having a shrinkable pouch according to the present disclosure is illustrated by FIGS. 8A, 8B, 9A and 9B, wherein at least one surgical tool 370 having a retracted inactive position and an extended active position is included. The surgical tool 370 may be a scalpel that includes a cutting edge 371 for cutting biological material at the surgical site. In the retracted position, the surgical tool 370 is disposed within a channel 374 having an opening 375 at the distal end of a sliding member 305, located in spaced relation to the at least one snare conduit 310, 310'. The proximal end of at least one surgical tool 370 is operably coupled to a corresponding surgical tool control, such as a handle or lever (not explicitly shown), which may be actuated by the surgeon to cause the surgical tool 370 to move between the distal extended position, as best shown in FIGS. 8B and 9B, and the retracted position as illustrated in FIGS. 8A and 9A.

Additionally or alternatively, the surgical tool 370 may be configured as an electrosurgical electrode for performing electrosurgical cutting, blending and/or coagulating at the operative site. In this configuration, the surgical tool 370 may be coupled to a source of electrosurgical energy such as, for example, an electrosurgical generator. The surgical tool 370 may be configured as a monopolar or bipolar electrosurgical electrode. As previously described above, the wire loop snare 320, 325' and surgical tool 370 operate in a cooperative relationship with a sliding member 305 for deployment such that wire loop snare 320, 325', surgical tool 370, and sliding member 305 move as a single unit with respect to a tubular housing 300 by actuation of the deployment control (not shown). Conversely, wire loop snare 320, 325' and surgical tool 370 may move independently from each other, and from sliding member 305 and tubular housing 300, by actuation of a tightening control (not shown) and the corresponding surgical tool control (not shown), respectively, as will be readily understood by the skilled artisan. Other surgical tools and/or end effectors are contemplated within the scope of the present disclosure, such as, without limitation, graspers, sealers, clamps, irrigators, suction tubes, and video or fiber optic endoscopes.

Figure 10A:
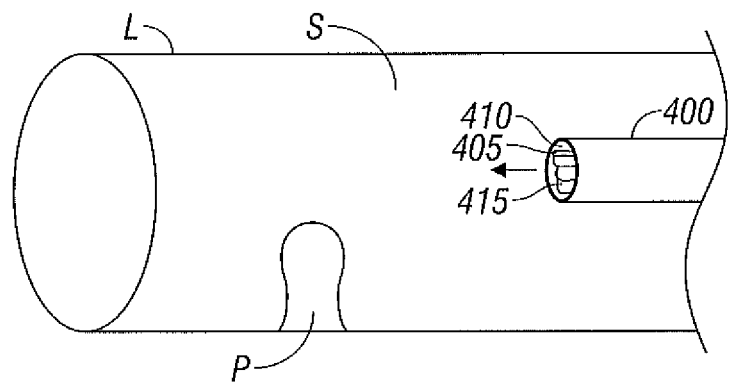
FIGS. 10A-I illustrate a method of polyp encapsulation and resection in accordance with the present disclosure.
Figure 10B:
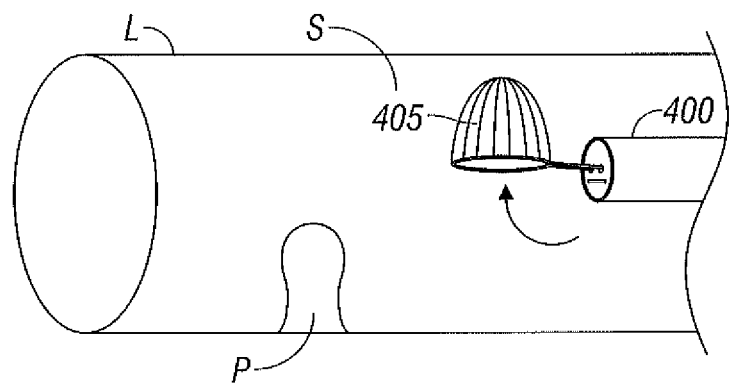
Figure 10C:
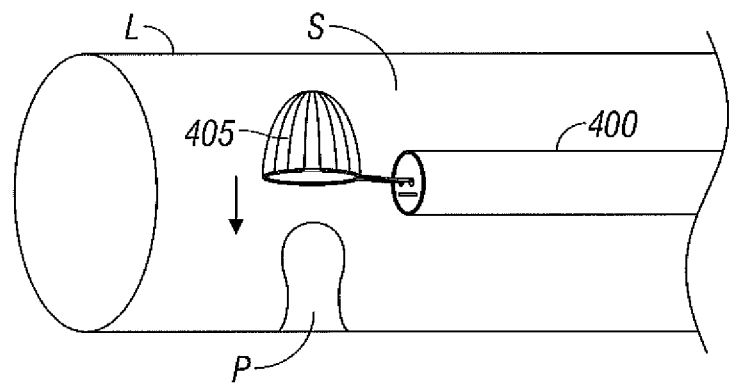
Figure 10D:
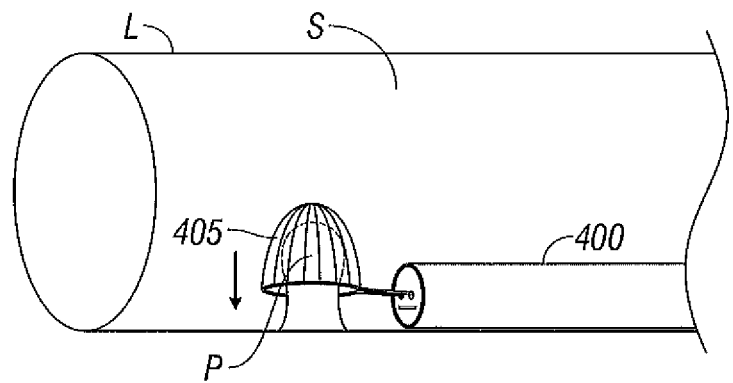
Figure 10E:
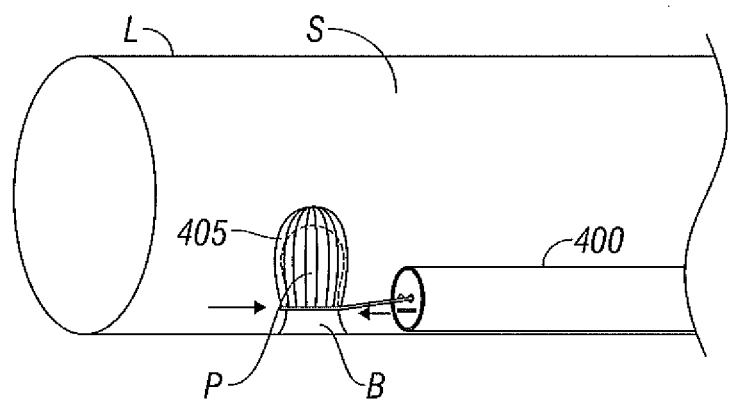
Figure 10F:
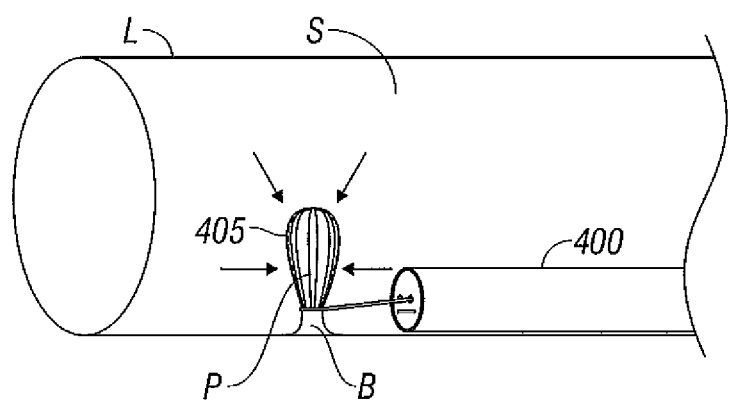
Figure 10G:
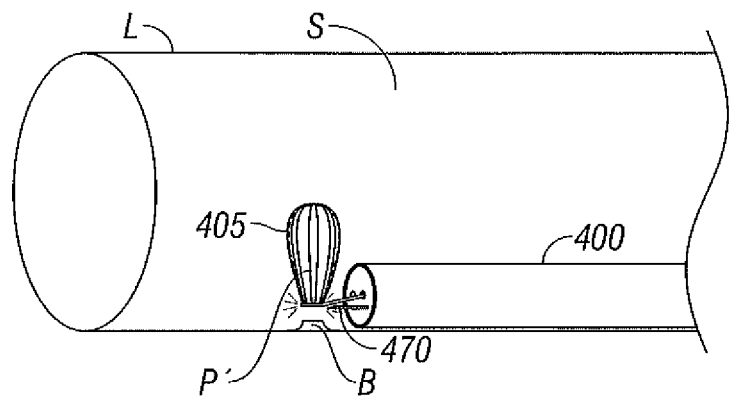

Turning now to FIGS. 10A-10I, there is illustrated a method for encapsulating and resecting biologic tissue, such as a polyp P that is situated at a surgical site S within a lumen L, which may be an esophagus, colon, intestine, urethra, blood vessel, or other tubular anatomic structure. The disclosed method includes the steps of providing at the surgical site S an endoscopic instrument 400 having a polyp encapsulation snare 405 that includes a shrinkable pouch 415 in accordance with the present disclosure as illustrated in FIG. 10A, deploying the polyp encapsulation snare 405 from a storage cavity 410 disposed within the instrument 400 as shown in FIG. 10B, positioning the deployed polyp encapsulation snare 405 adjacent to the polyp P as illustrated in FIG. 10C, positioning the polyp encapsulation snare 405 over the polyp P such that the pouch 415 envelops the polyp P as depicted in FIG. 10D, tightening the snare 405 around the base B of polyp P as shown in FIG. 10E, shrinking the pouch 415 to encapsulate and optionally or alternatively reduce the size of the polyp as shown in FIG. 10F, providing an electrosurgical signal to the wire loop snare to sever the polyp P from the lumen L and/or from the polyp base B as shown in FIG. 10G, and withdrawing the endoscopic instrument 400 including the snare 405 containing the resected polyp P' from surgical site.

The shrinking step of the disclosed method may additionally or alternatively include at least one of the steps of applying electrical energy to the pouch 415, applying thermal energy to the pouch 415, and/or applying a chemical to the pouch 415. Additionally or alternatively, disclosed method includes the step of exposing the pouch 415 to body heat and/or bodily fluids to effectuate shrinkage of the pouch 415.

Figure 10H:
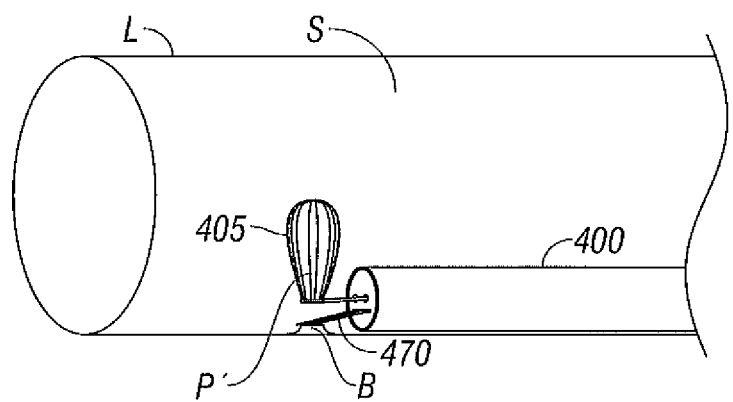
Figure 10I:
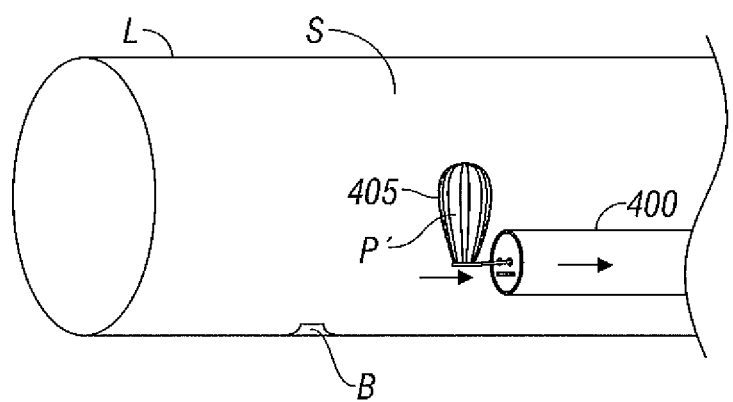

The provided method can additionally include coagulating or cauterizing the operative site substantially concurrently with, or subsequent to, the step of severing the polyp. Optionally or additionally, the method includes the step of extending from the endoscopic instrument 400 a surgical instrument 420 and performing at least one electrosurgical or non-electrosurgical procedure therewith at the operative site as depicted in FIG. 10H. It is envisioned the steps of the above method may be performed in a different order than that described, and/or the operations performed within an individual step or steps may be desirably be combined into a single step without departing from the scope and spirit of the method disclosed herein.

Further variations of the above-disclosed and other features and functions, or alternatives thereof, may be desirably combined into many other different systems, instruments and applications. Various presently unforeseen or unanticipated alternatives, modifications, variations or improvements therein may be subsequently made by those skilled in the art, which are also intended to be encompassed by the following claims.

What is claimed is:

1. A method for encapsulating and resecting tissue from a patient, comprising the steps of:
   providing a polyp encapsulation device, wherein the polyp encapsulation device includes a wire loop snare including a longitudinal slot defined therein and a shrinkable pouch slidingly disposed within the longitudinal slot and including at least one heating element;
   positioning the polyp encapsulation device over the tissue to be encapsulated such that the shrinkable pouch envelops the tissue;
   tightening the wire loop snare around the tissue to be encapsulated;
   heating the shrinkable pouch to shrink to encapsulate the tissue; and
   resecting the tissue.

2. The method according to claim 1, wherein the polyp encapsulation device further includes a surgical instrument having a retracted inactive position and an extended active position.

3. The method according to claim 2, wherein the resecting step further comprises:
   extending the surgical instrument to the operative position; and
   severing the tissue from the patient with the surgical instrument.

4. The method according to claim 2, wherein the resecting step further comprises:
   extending the surgical instrument to the operative position;
   providing electrosurgical energy to the surgical instrument; and
   electrosurgically cutting the tissue from the patient with the surgical instrument.

5. The method according to claim 1, wherein the resecting step is performed by providing an electrosurgical signal to the wire loop snare.

6. A polyp encapsulation device, comprising:
   a wire loop snare providing a longitudinal slot defined therein; and
   a shrinkable pouch including at least one heating element and having a closed end and an open end, wherein the open end is slidably disposed within the longitudinal slot of the wire loop snare;
   wherein the shrinkable pouch is adapted to electrically insulate the polyp tissue from surrounding tissue.

7. The polyp encapsulation device according to claim 6, wherein the heating elements cause the shrinkable pouch to shrink; and
   the wire loop snare further includes at least one coupling member that connects the heating elements to a source of shrinking energy.

8. The polyp encapsulation device according to claim 7, wherein the shrinkable pouch is constructed from material selected from the group consisting of heat-shrinkable material, electrically-shrinkable material, and chemically-shrinkable material.

9. The polyp encapsulation device according to claim 7, wherein the heat-shrinkable material is selected from the group consisting of polyethylene, cross-linked polyolefin, and shape memory alloy.

10. The polyp encapsulation device according to claim 7, wherein the shrinkable material has an optical transmissivity selected from the group consisting of substantially transparent, substantially translucent, and substantially opaque.

11. The polyp encapsulation device according to claim 7, wherein the heating elements are constructed from material selected from the group consisting of resistance wire, shape memory alloy, Nichrome, and Nitinol.

12. The polyp encapsulation device according to claim 6, further comprising at least one surgical tool having a retracted inactive position and an extended active position.

13. The polyp encapsulation device according to claim 12, wherein the at least one surgical tool is selected from the group consisting of a scalpel, a grasper, a sealer, clamps, an irrigator, a suction tube, a video endoscope, and a fiber optic endoscope.

14. The polyp encapsulation device according to claim 12, wherein the at least one surgical tool comprises an electrosurgical electrode for performing an electrosurgical procedure selected from the group consisting of cutting, blending, and coagulating.

15. The polyp encapsulation device according to claim 6, wherein the wire loop snare includes an electrosurgical electrode for performing an electrosurgical procedure selected from the group consisting of cutting, blending, and coagulating.

16. A system for encapsulating polyp tissue, comprising:
   an endoscopic instrument adapted for insertion into a lumen, the endoscopic instrument further comprising:
   a wire loop snare including a longitudinal slot defined therein; and
   a pouch responsive to shrink activation energy to shrink from a first configuration to at least one smaller configuration, the pouch including at least one heating element and a closed end and an open end, wherein the open end is slidably disposed within the longitudinal slot of the wire loop snare, the pouch being adapted to electrically insulate polyp tissue from surrounding tissue; and a source of shrink activation energy electro-operably coupled to the pouch.

17. The system according to claim 16, wherein the endoscopic instrument includes a surgical tool having a retracted inactive position and an extended active position.

18. The system according to claim 16, further comprising:
a source of electrosurgical energy; and
an electrosurgical electrode;
wherein the source of electrosurgical energy and the electrosurgical electrode are electro-operably coupled.

19. The system according to claim 16, wherein the endoscopic instrument includes an electrosurgical electrode having a retracted inactive position and an extended active position;
a source of electrosurgical energy;
wherein the source of electrosurgical energy and the electrosurgical electrode are electro-operably coupled.

20. The system according to claim 16, wherein the wire loop snare includes an electrosurgical electrode and the system further comprises:
a source of electrosurgical energy;
wherein the source of electrosurgical energy and the wire loop snare are electro-operably coupled.

* * * * *